(12) United States Patent
Ushiyama

(10) Patent No.: US 7,141,387 B2
(45) Date of Patent: Nov. 28, 2006

(54) MICROORGANISM CULTURE MEDIUM

(75) Inventor: Masashi Ushiyama, Yokohama (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 11/179,098

(22) Filed: Jul. 12, 2005

(65) Prior Publication Data

US 2006/0008867 A1    Jan. 12, 2006

(30) Foreign Application Priority Data

Jul. 12, 2004    (JP) .............................. 2004-204336

(51) Int. Cl.
*C12N 1/16*    (2006.01)
*C12Q 1/04*    (2006.01)

(52) U.S. Cl. .......................... 435/34; 435/7.2; 435/29; 435/255.7

(58) Field of Classification Search ................ 435/7.2, 435/29, 34, 253.6, 255.7
See application file for complete search history.

(56) References Cited

U.S. PATENT DOCUMENTS 5,821,066 A * 10/1998 Pyle et al. ................... 435/7.2

FOREIGN PATENT DOCUMENTS

| JP | 2001-231541 | | 8/2001 |
|---|---|---|---|
| JP | 231541 | * | 8/2001 |
| JP | 2001-245693 | | 9/2001 |
| JP | 245693 | * | 9/2001 |

OTHER PUBLICATIONS

F. P. Altman, "Tetrazolium Salts and Formazans", Gustav Fischer Verlag Stuttgart, New York, (1976), 23-25.
E. Seidler, "Progress in Histochemistry and Cytochemistry", 1991, 24(1), 21-23.
"Polarography". McGraw-Hill Encyclopedia of Science & Technology 5$^{th}$ Edition, 1982, 597-660.

* cited by examiner

*Primary Examiner*—Herbert J. Lilling
(74) *Attorney, Agent, or Firm*—Hamre, Schumann, Mueller & Larson, P.C.

(57) ABSTRACT

A microorganism culture medium comprising a derivative A' of a chromogen A, and a chromogen B, where the chromogen A is a chromogen being oxidized to a colorant, and the chromogen B is a chromogen being reduced to a colorant. The derivative A' acts as a substrate of an enzyme generated when a microorganism is growing, and is then converted to the chromogen A, and the derivative A' and the chromogen B are substantially not colored in the culture medium unless a microorganism is inoculated.

7 Claims, 1 Drawing Sheet

MICROORGANISM CULTURE MEDIUM

BACKGROUND OF THE INVENTION

1. Field of the Invention

The present invention relates to a medium for culturing microorganisms. More specifically, it relates to a medium for examination of foods or the environment, which can be used to detect microbial contamination in foods or the environment more quickly than conventional standard media.

2. Description of Related Art

The conventional microorganism examination is carried out in the following manner. In the case of yeasts and molds, first a powder agar medium is dissolved, autoclaved and poured into Petri dish, which is then cooled and solidified to keep the surface dry. The predetermined amount of a test sample such as a homogenate of foods is applied on the above prepared agar medium and incubated at 25° C. for maximum 7 days, and the number of grown colonies is then counted. For enumeration of yeasts and molds in the environment, a predetermined portion of a test object is wiped with a cotton swab or gauze, and then any microorganism caught on the swab or gauze is washed with sterilized water to be suspended in the sterilized water. This homogenate is applied on the above prepared agar medium and incubated, and then the number of grown colonies is counted. In the case of total viable counts, first a powder agar medium is dissolved and autoclaved, and is then kept at approx. 45° C. A predetermined quantity of this agar medium is poured into sterilized Petri dish, and mixed with 1 ml of a test sample such as a homogenate of foods, which has been pre-poured in the Petri dish, and is then solidified. Incubation is carried out at 35° C. for 2 days, and the number of grown microorganism colonies is counted. Thus, the conventional method of examining microorganisms requires 7 days of incubation for yeasts and molds enumeration, and 2 days for total viable count.

As a culture medium that can detect growing microorganism colonies by using a chromogenic reagent, a medium using an indole derivative is described, for example, in Reference 1, and a medium using TTC (2,3,5-triphenyl tetrazolium chloride) as a tetrazolium salt is described, for example, in Reference 2.

Reference 1: Japanese Tokkyo Kokai Koho (Un-Examined Patent Publication) 2001-231541

Reference 2: Japanese Tokkyo Kokai Koho 2001-245693

SUMMARY OF THE INVENTION

The present invention aims to provide a microorganism culture medium that can shorten the conventional incubation time of 7 days for yeasts and molds enumeration and 2 days for total viable counts, and can achieve quantitative accuracy of the test results in a short time.

Various studies have been carried out to solve the above problem to find that it is effective to add a derivative A' of a chromogen A, and a chromogen B; wherein the chromogen A is a chromogen that is oxidized to form a colorant, and the chromogen B is a chromogen that is reduced to form a colorant. The derivative A' acts as a substrate of an enzyme generated when a microorganism is growing, and then is converted to the chromogen A; and the derivative A' and the chromogen B are substantially not colored in the culture medium unless a microorganism is inoculated. This enables a quick detection of growth of microorganisms; namely, coloring occurs in about 2 days in the case of yeasts and molds enumeration, and within 24 hours in the case of total viable counts.

The present invention includes:

(1) A microorganism culture medium comprising a derivative A' of a chromogen A, and a chromogen B, wherein the chromogen A is a chromogen that is oxidized to form a colorant, and the chromogen B is a chromogen that is reduced to form a colorant, the derivative A' acts as a substrate of an enzyme generated when a microorganism is growing, and is then converted to the chromogen A, and the derivative A' and the chromogen B are substantially not colored in the culture medium unless a microorganism is inoculated.

(2) The microorganism culture medium described in the above item (1), wherein the derivative A' of the chromogen A is an oxyindole derivative or a halogen-substituted oxyindole derivative.

(3) The microorganism culture medium described in the above item (1), wherein the chromogen B is a tetrazolium salt having the half wave potential of 300 mv or less at its absolute value.

(4) The microorganism culture medium described in the above item (2), wherein the oxyindole derivative or the halogen-substituted oxyindole derivative is an acetic acid ester, a fatty acid ester, a phosphoric acid ester, a sulfuric acid ester or a glucoside.

(5) The microorganism culture medium described in the above item (1), wherein the medium is a sheet type medium.

(6) The microorganism culture medium described in the above item (1), wherein the medium is an agar medium.

(7) A method for detecting microorganisms using the medium described in the above item (1).

According to the present invention, examination time of microorganisms can be shortened, so that the number of microorganisms can be determined in 2 days in the case of yeasts and molds enumeration, and within 24 hours in the case of total viable counts. Especially, examination time for yeasts and molds enumeration is greatly shortened.

DETAILED DESCRIPTION OF THE INVENTION

Figure 1:
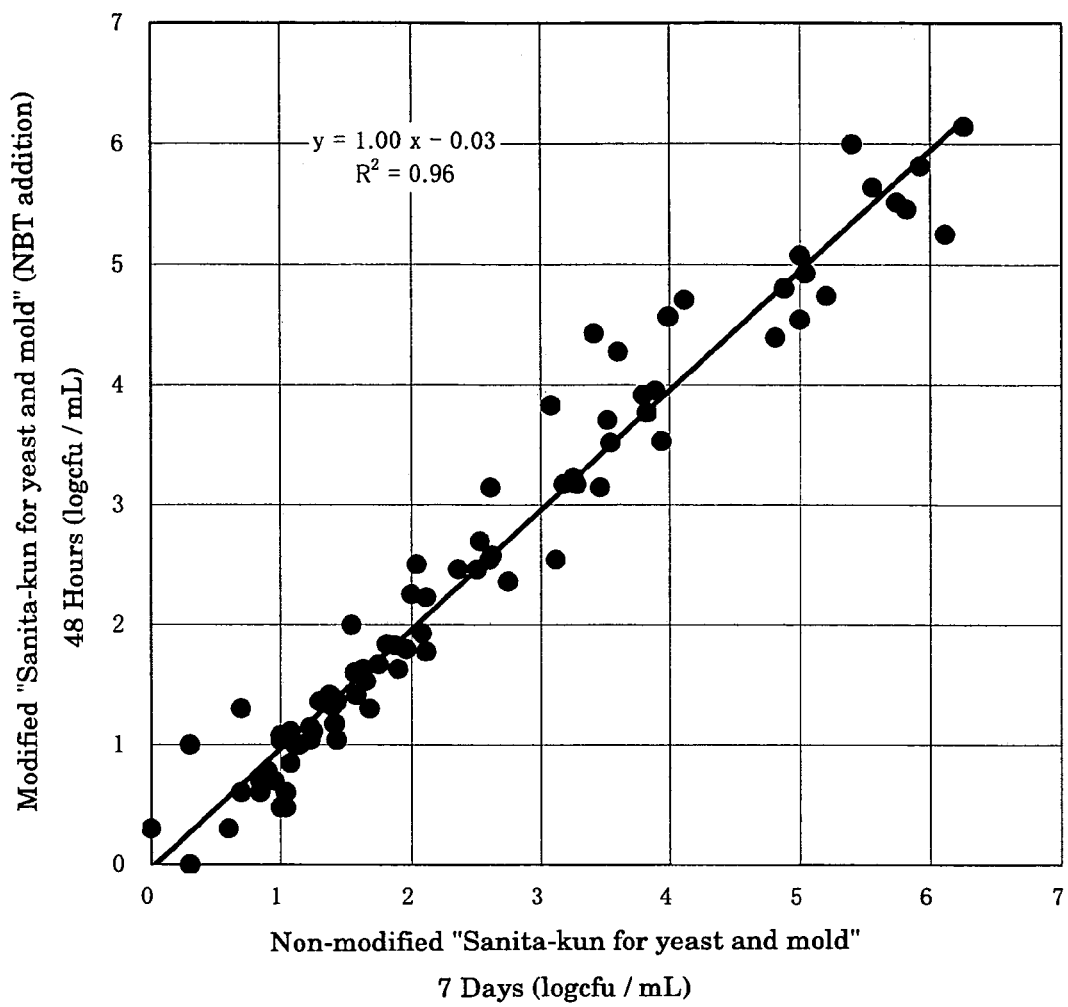
FIG. 1 shows the comparison between 48-hour incubation of modified "Sanita-kun for yeast and mold" to which Nitro Blue Tetrazolium was added and 7-day incubation of non-modified "Sanita-kun for yeast and mold".

The present invention is characterized in that;

the chromogen A, which is unstable per se and converted to a colorant by oxidation, is kept in a stabilized condition as the derivative A', which acts as a substrate of an enzyme generated when a microorganism is growing;

the derivative A' coexists with the chromogen B which is converted to a colorant by reduction;

and when the microorganism inoculated into the medium is growing to make colonies while generating an enzyme, the derivative A' is decomposed into the chromogen A by the generated enzyme; further the chromogen A is sharply colored by a redox reaction with the chromogen B;

so that the colonies of microorganism can be detected in a short time.

In the description of "derivative A' of chromogen A" and "chromogen B", the meaning of the phrase "substantially not colored in the culture medium unless the microorganism is inoculated" is as follows. That is, the derivative A' of the chromogen A is never to be decomposed to the chromogen A and causes no color reaction unless an enzyme generated from microorganisms is present. The derivative A' should not participate in a redox reaction with the chromogen B. A derivative that causes background color of the medium without microorganism inoculation is not desirable as the derivative A', because such a derivative makes it difficult to distinguish the color of growing microorganism colonies from the background color. However, if a derivative causes slight background color that is well distinguishable from the color of the inoculated microorganism, such a derivative can be used as the derivative A' without any problem and is acceptable for the purposes of the present invention.

The "colorant" in the present invention can be any material that colors the microbial colonies. These may be pigments, dyes, etc.

Examples of the derivative A' according to the present invention include various derivatives of oxyindole or halogen-substituted oxyindole. These derivatives are enzymatically hydrolyzed to oxyindole or halogen-substituted oxyindole as the chromogen A, which is further oxidatively polymerized to form a colored indigo compound. The speed of the oxidative polymerization can be accelerated with the aid of an oxidizer to show quicker coloring. Use of the chromogen B, which is reduced to a colorant, as an oxidizer further can accelerate the coloring. When detecting yeasts and molds or total viables, it is preferred to use, as the derivative A', a derivative acting as a substrate of an enzyme such as esterase, lipase, phosphatase, sulfatase or glucosidase, which microorganisms universally have. Examples of such a derivative include indoxyl butyrate, 5-bromo-4-chloro-3-indoxyl acetate or 5-bromo-4-chloro-3-indoxyl phosphate.

Examples of the chromogen B that is reduced to a colorant include tetrazolium salts.

In the combined use of the derivative of oxyindole or halogen-substituted oxyindole and tetrazolium salt, microorganisms hydrolyze the derivative of oxyindole or halogen-substituted oxyindole to form oxyindole or halogen-substituted oxyindole. The resultant oxyindole or halogen-substituted oxyindole is oxydatively polymerized by oxygen to form a colored indigo compound. The tetrazolium salt also oxidizes the oxyindole or halogen-substituted oxyindole. While the polymerization is accelerated, the tetrazolium salt itself is reduced to form colored formazan. Further, the tetrazolium salt is reduced by metabolism of the microorganisms.

When combining the chromogen A that is oxidized to a colorant and the chromogen B which is reduced to a colorant, it is preferable that both of these chromogens form the same type of colorants. This is because the colors have an additive effect with each other to enhance the visibility.

Many of the tetrazolium salts can be reduced by metabolism of microorganisms to form colored formazans. In order to act as an oxidizer at an ordinary incubation temperature of 25–35° C. those having a low redox potential are preferable. "Half wave potential ($E_{1/2}$)" measured by polarography is used to express a value of redox potential. The method for polarographic measurement of the half wave potential ($E_{1/2}$) is detailed, for example, in "Jikken Kagaku Koza (Lectures of Experimental Chemistry), 4th. edition", edited by The Chemical Society of Japan, published by MARUZEN Co. Ltd., Vol. 9, pages 297–9, "6.4.4 Polarography". The value of the half wave potential ($E_{1/2}$) is indicated by positive number in some references and by negative number in other references. Therefore, its absolute value should be adopted as this criterion. In the case of using a tetrazolium salt as the chromogen B in the present invention, the absolute value of its half wave potential is preferably 300 mv or less. Half wave potentials of various tetrazolium salts are described in detail in E. Seidler, "Progress in Histochemistry and Cytochemistry", (1991), 24(1), pages 21–3, (especially in "Table 5" on page 22), or in F. P. Altman, "Tetrazolium Salts and Formazans", (1976), published by Gustav Fischer Verlag, pages 23–5, (especially in "Table 7" on page 24). In the present invention, a preferable tetrazolium salt can be selected based on the above criterion of the absolute value of half wave potential ($E_{1/2}$). (Hereinafter, the expression "half wave potential" or "$E_{1/2}$" means its absolute value.)

Examples of these suitable tetrazolium salts are given below. (CAS registry number is indicated in brackets [ ].)

Neotetrazolium Blue [298-95-3],
Chemical name:
3,3'-(1,1'-biphenyl-4,4'-diyl)-bis(2,5-diphenyl-2H-tetrazolium chloride),
$E_{1/2}$=170 mv
INT [146-68-9],
Chemical name:
2-(4-iodophenyl)-3-(4-nitrophenyl)-5-phenyl-2H-tetrazolium chloride,
$E_{1/2}$=90 mv
Tetrazolium Blue [1871-22-3],
Chemical name:
3,3'-[3,3'-dimethoxy-(1,1'-biphenyl)-4,4'-diyl]-bis(2,5-diphenyl-2H-tetrazolium chloride
$E_{1/2}$=80 mv
Nitro Blue Tetrazolium [298-83-9],
Chemical name:
3,3'-[3,3'-dimethoxy-(1,1'-biphenyl)-4,4'-diyl]-bis[2-(4-nitrophenyl)-5-phenyl-2H-tetrazolium chloride],
$E_{1/2}$=50 mv
Tetranitrotetrazolium Blue [1184-43-6]
Chemical name:
3,3'-(3,3'-dimethoxy-4,4'-biphenylene)-bis[2,5-bis(p-nitrophenyl)-2H-tetrazolium chloride],
$E_{1/2}$=50 mv When using tetrazolium salt as the chromogen B, it is preferable to select a tetrazolium salt having the absolute value of the half wave potential of 300 mv or less. However, it is experimentally confirmed that a certain tetrazolium salt meeting this half wave potential criterion is colored in the medium without microorganism inoculation. This exception is MTT [2348-71-2] having $E_{1/2}$ of 110 mv, which is not suitable as the chromogen B according to the invention. Contrary to this, when the chromogen B is INT having lower $E_{1/2}$ (90 mv) than MTT, no coloring occurs in the medium unless a microorganism is inoculated. Accordingly, this criterion of $E_{1/2}$ being 300 mv or less is proper for carrying out the present invention. This criterion is supported as long as substantially no coloring occurs unless a microorganism is inoculated when the derivative A' and the chromogen B are mixed in the medium.

The present invention can be carried out by adding to a nutrient microorganism culture medium the derivative A' of the chromogen A and the chromogen B both fulfilling the above requirements. The nutrient to be contained in the medium can be selected appropriately depending on the microorganism to be incubated. When the present invention is used for culturing yeasts and molds, an appropriate nutrient is glucose, yeast extract, peptone, malt extract, potato extract or a mixture of these two or more. When the present invention is used for culturing total viables, an appropriate nutrient is glucose, yeast extract, peptone, meat extract, a salt or a mixture of these two or more. The shape of the medium is not limited, and it may be an agar medium, or a sheet type medium for a simple examination of microorganism.

For preparing an agar medium for yeasts and molds, to a medium composition such as potato dextrose agar, Sabouraud agar, yeast mold agar or the like are added an oxyindole derivative or a halogen-substituted oxyindole derivative as the derivative A', such as indoxyl butyrate, 5-bromo-4-chloro-3-indoxyl acetate acetate, or 5-bromo-4-chloro-3-indoxyl phosphate; and a tetrazolium salt as the chromogen B to prepare an agar medium for yeasts and molds.

For preparing an agar medium for total viable counts, to a medium composition such as plate count agar, tryptic soy agar, soybean-casein digest agar or the like are added an oxyindole derivative or a halogen-substituted oxyindole derivative as the derivative A', such as indoxyl butyrate, 5-bromo-4-chloro-3-indoxyl acetate acetate, or 5-bromo-4-chloro-3-indoxyl phosphate; and a tetrazolium salt as the chromogen B to prepare an agar medium for total viable counts.

For preparing a sheet type medium, to a sheet type medium for yeasts and molds described, for example, in Japanese Tokkyo Kokai Koho 2001-231541, or a sheet type medium for total viable counts described, for example, in Japanese Tokkyo Kokai Koho 2001-245693 are added an oxyindole derivative or a halogen-substituted oxyindole derivative as the derivative A', such as indoxyl butyrate, 5-bromo-4-chloro-3-indoxyl acetate acetate, or 5-bromo-4-chloro-3-indoxyl phosphate; and a tetrazolium salt as the chromogen B to prepare a sheet type medium for yeasts and molds or total viable counts.

An effective amount of the derivative A' to be contained in the medium is 0.01 $g/m^2$ or more for the sheet type medium and 0.002 g/L or more for the agar medium, with no special upper limit set. The appropriate content may be determined by taking the economical efficiency into consideration.

An effective amount of the chromogen B to be contained in the medium is 0.005 $g/m^2$ or more for the sheet type medium and 0.002 g/L or more for the agar medium. And 0.1 $g/m^2$ or less for the sheet type medium and 0.05 g/L or less for the agar medium are preferable in that the background is not colored excessively.

EXAMPLES

The present invention will be described in more detail by the following Examples, which no way limit the present invention. "Sanita-Kun (commercial name) for yeast and mold" (manufactured by Chisso Corporation) used in the Examples is a sheet type medium having the following construction.

"Sanita-Kun for Yeast and Mold"

35 g of a polyvinyl alcohol having a saponification ratio of 89% and a molecular weight of 83,000 was added to 0.3 L of water and dissolved by heating. The whole mixture was then applied on a 0.5 m by 1 m sheet of polyester film having a thickness of 20 μm, and dried at 120° C. for 6 minutes to form the first water-soluble polymer layer. On the above obtained first layer, a solution of 15 g of the above polyvinyl alcohol, 1.2 g of yeast extract, 4.5 g of glucose and 0.375 g of chloramphenicol dissolved in 0.25 L of water was applied in whole, and dried at 110° C. for 7 minutes to form the second water-soluble polymer layer. On the above second layer, a solution of 5 g of the above polyvinyl alcohol, 0.4 g of yeast extract, 1.5 g of glucose, 0.125 g of chloramphenicol and 0.03 g of 5-bromoindoxyl acetate dissolved in 0.1 L of water was applied in whole. Then a nylon meltblown nonwoven fabric having basis weight of 65 $g/m^2$ and air permeability of 110 $L/(m^2 \cdot sec)$ was laminated on it and dried at 100° C. for 30 seconds. A solution of 20 g of peptone dissolved in 1 L of water was applied on the above nonwoven fabric using 60 mesh of a rotogravure roll having 60 mesh of pyramid cells, which was then dried at 100° C. for 20 seconds. The laminated medium material thus obtained was cut into 45 mm by 45 mm pieces. Each piece was adhered on a white polyester adhesive sheet (substrate), which was then covered with a polypropylene film, and sterilized with ethylene oxide gas to prepare "Sanita-Kun for yeast and mold".

Example 1

Preparation of a Sheet Type Medium Using "Sanita-kun for Yeast and Mold"

The sheet type medium "Sanita-kun for yeast and mold" (manufactured by Chisso Corporation) containing 5-bromoindoxyl acetate as the derivative A' was used. It was uncovered, and 0.5 mL of Nitro Blue Tetrazolium ethanol solution (concentration 0.1 mg/mL) was added onto the surface of the nonwoven fabric, which was then dried at 50° C. for 5 hours. Thus, a modified "Sanita-kun for yeast and mold" with the addition of Nitro Blue Tetrazolium was prepared.

Example 2

Test of the Sheet Type Medium Using "Sanita-kun for Yeast and Mold"

A homogenate testing sample was prepared either by adding a 9-fold amount of sterilized water to each food, stomached and diluting to an appropriate concentration, or by wiping each testing object with a cotton swab, and putting the swab into 10 mL of sterilized water with vigorous shaking. 1 mL of the homogenate sample was added to the modified "Sanita-kun for yeast and mold" prepared in Example 1. For comparison, 1 mL of the same sample was added to "Sanita-kun for yeast and mold" (non-modified). The incubation was carried out at 25° C. for 48 hours in the modified "Sanita-kun for yeast and mold" and for 7 days in "Sanita-kun for yeast and mold" (non-modified). The number of the grown blue colonies in each medium was counted for comparison. As shown in FIG. 1, the results of the count in both cases are approximately the same. The regression equation is;

"$y=1.00x-0.03$", (y: the count of 48-hour incubation in the modified "Sanita-kun for yeast and mold"; x: the count of 7-day incubation in "Sanita-kun for yeast and mold" (non-modified).); its correlation factor ($r^2$) is 0.96.

Example 3

Preparation of a Sheet Type Medium for Yeasts and Molds 14 g of a polyvinyl alcohol having a saponification ratio of 89% and a molecular weight of 83,000 was added to 0.12 L of water and dissolved by heating. The whole mixture was then applied on a 0.4 m by 0.5 m sheet of polyester film having a thickness of 20 μm, and dried at 120° C. for 6 minutes to form the first water-soluble polymer layer. On the above obtained first layer, a solution of 6 g of the above polyvinyl alcohol, 0.64 g of yeast extract, 2.4 g of glucose and 0.2 g of chloramphenicol dissolved in 0.1 L of water was applied in whole, and dried at 110° C. for 7 minutes to form the second water-soluble polymer layer. On the above second layer, a solution of 2 g of the above polyvinyl alcohol, 0.012 g of 5-bromoindoxyl acetate and 0.005 g of Nitro Blue Tetrazolium dissolved in 0.04 L of water was applied in whole. Separately, a solution of 20 g of peptone dissolved in 1 L of water was applied on a nylon melt-blown nonwoven fabric having basis weight of 65 g/m$^2$ and air permeability of 110 L/(m$^2$·sec) using a rotogravure roll having 60 mesh of pyramid cells, which was then dried at 100° C. for 20 seconds. Then, the thus pre-treated nylon melt-blown nonwoven fabric was further laminated and dried at 100° C. for 30 seconds to obtain a laminated medium material. The laminated medium material thus obtained was cut into 45 mm by 45 mm pieces. Each piece was adhered on the center of a white polyester adhesive sheet (manufactured by Kyowa Limited, thickness 100 μm, acryl adhesive is applied thereon, cut into 80 mm by 85 mm pieces). The sheet was covered with a 80 mm by 85 mm sheet of polypropylene film having a thickness of 0.06 mm in such a way as to make an uncovered portion of 5 mm along the 85 mm direction, and sealed with a back sealing tape (manufactured by Kyowa Limited, width 9 mm) in such a way as to cover the uncovered portion of the adhesive sheet, which was then sterilized with ethylene oxide gas to prepare a sheet type medium for yeasts and molds.

Example 4

Test of the Sheet Type Medium for Yeasts and Molds

Comparison was made between the sheet type medium prepared in Example 3 and "Sanita-kun for yeast and mold" (non-modified) in the same manner as in Example 2. The colony counts in the 48-hour incubation of the sheet type medium prepared in Example 3 and in the 7-day incubation of "Sanita-kun for yeast and mold" (non-modified) were approximately the same, like the comparison result of Example 2.

Example 5

Variations of Sheet Type Media for Yeasts and Molds

Sheet type media for yeasts and molds were prepared in the same manner as in Example 3, except for using indoxyl acetate, indoxyl butyrate, indoxyl phosphate and 5-bromo-4-chloro-3-indoxyl acetate, respectively, instead of 5-bromoindoxyl acetate. Comparison tests were carried out in the same manner as in Example 2. The testing results were also the same as Example 2.

Example 6

Agar Medium for Total Viable Counts

Plate count agar was dissolved in water and autoclaved, and then cooled to 50° C. to prepare an agar medium. To 1 L of this agar medium were added 1 mL each of ethanol solutions of 0.06 mg/mL indoxyl acetate and 0.025 mg/mL Nitro Blue Tetrazolium and stirred.

A 9-fold amount of sterilized physiological saline was added to each of various foods and treated with a stomacher, which was then diluted to an appropriate concentration to prepare a homogenate testing sample. 1 mL of the homogenate sample was poured into Petri dish, and then mixed with the above agar medium to which indoxyl acetate and Nitro Blue Tetrazolium were added. For comparison, the same sample was mixed with the agar medium to which indoxyl acetate and Nitro Blue Tetrazolium were not added. After each agar was solidified, the incubation was carried out at 35° C. for 20 hours in the agar with indoxyl acetate and Nitro Blue Tetrazolium, and for 48 hours in the agar without indoxyl acetate and Nitro Blue Tetrazolium. The grown colony counts of both cases were approximately the same.

Example 7

Variations of Agar Media for Total Viable Count

Agar media for total viable count were prepared in the same manner as in Example 6, except for using each dimethylformamide solution of 5-bromo-6-chloro-3-indoxyl acetate, 5-bromo-6-chloro-3-indoxyl phosphate and 5-bromo-6-chloro-3-indoxyl butyrate; and each ethanol solution of 6-chloro-3-indoxyl acetate, 6-chloro-3-indoxyl phosphate and 6-chloro-3-indoxyl butyrate, respectively, instead of the ethanol solution of indoxyl acetate. The tests were carried out in the same manner as in Example 6. The testing results were the same as Example 6. Further, Nitro Blue Tetrazolium used in Example 6 was replaced by INT and a test was conducted again in the same manner as in Example 6. The colonies were purple colored, and the results were also the same as Example 6.

Example 8

Preparation of a Sheet Type Medium for Total Viable Counts 12 g of a polyvinyl alcohol having a saponification ratio of 89% and a polymerization degree of 1,700 was added to 0.1 L of water and dissolved by heating. Then the mixture was applied on a 0.4 m by 1 m polyester film having a thickness of 20 μm, and dried at 120° C. for 5 minutes to form a film layer. On this film layer, a solution of 6 g of the above polyvinyl alcohol, 1.24 g of peptone, 0.25 g of meat extract, 0.32 g of yeast extract, 0.04 g of sodium carbonate and 0.16 g of glucose dissolved in 0.1 L of water was applied and dried at 110° C. for 7 minutes. Further on this layer, a solution of 2 g of the above polyvinyl alcohol, 0.02 g of 5-bromo-4-chloro-3-indoxyl acetate and 0.01 g of Nitro Blue Tetrazolium dissolved in 0.04 L of water was laminated. Separately, a solution of 15 g of peptone and 40 g of disodium hydrogenphosphate dissolved in 1 L of water was applied on a nylon melt-blown nonwoven fabric having basis weight of 65 g/m$^2$ and air permeability of 110

L/(m²·sec) using a rotogravure roll having 60 mesh of pyramid cells, followed by drying at 100° C. for 20 seconds. The thus pre-treated nylon melt-blown nonwoven fabric was further laminated and dried at 100° C. for 30 seconds to obtain a laminated medium material. This laminate was cut into 45 mm by 45 mm pieces. Each piece was adhered on the center of a white polyester adhesive sheet (manufactured by Kyowa Limited, thickness 100 μm, acryl adhesive is applied thereon, cut into 80 mm by 85 mm pieces). The sheet was covered with a 80 mm by 85 mm sheet of polypropylene film having a thickness of 0.06 mm in such a way as to make an uncovered portion of 5 mm along the 85 mm direction, and sealed with a back sealing tape (manufactured by Kyowa Limited, width 9 mm) in such a way as to cover the uncovered portion of the adhesive sheet, which was then sterilized with ethylene oxide gas to prepare a sheet type medium for total viable counts.

Example 9

Test of the Sheet Type Medium for Total Viable Counts

A 9-fold amount of sterilized physiological saline was added to each of various foods and stomached, which was then diluted to an appropriate concentration to prepare a homogenate testing sample. 1 mL of the homogenate sample was added onto the media prepared in Example 8 and also Petri dish which was then mixed with a plate count agar medium, and incubated at 35° C. Comparison was made to find out that the colony counts of 20-hour incubation of the medium in Example 8 and 48-hour incubation of the plate count agar medium were approximately the same.

Example 10

Variations of Sheet Type Media for Total Viable Counts

Sheet type media for total viable counts were prepared in the same manner as in Example 8, except for using indoxyl acetate, indoxyl butyrate, indoxyl phosphate and 5-bromoindoxyl acetate, respectively, instead of 5-bromo-4-chloro-3-indoxyl acetate. Comparison tests were carried out in the same manner as in Example 9. The testing results were the same as Example 9.

Example 11

Second Variations of Sheet Type Media for Yeasts and Molds

Sheet type media for yeasts and molds were prepared in the same manner as in Example 3, except for using Neotetrazolium Blue, INT and Tetranitrotetrazolium Blue, respectively, instead of Nitro Blue Tetrazolium. Comparison tests were carried out in the same manner as Example 4. The testing results were also the same as in Example 4. The colony color of these sheet type media was light blue in the case of Neotetrazolium Blue, purple in the case of INT, and dark blue between indigo in the case of Tetranitrotetrazolium Blue.

Example 12

Second Variations of Sheet Type Media for Total Viable Counts

Sheet type media for total viable counts were prepared in the same manner as in Example 7, except for using Neotetrazolium Blue, INT and Tetranitrotetrazolium Blue, respectively, instead of Nitro Blue Tetrazolium. Comparison tests were carried out in the same manner as in Example 9. The testing results were also the same as Example 9. The colony color of these sheet type media was light blue in the case of Neotetrazolium Blue, purple in the case of INT, and dark blue between indigo in the case of Tetranitrotetrazolium Blue.

The medium of the present invention can be advantageously used for detecting microorganism contamination in foods or the environment quicker than conventional standard media.

While a detailed description of the present invention has been provided above, the present invention is not limited to the detailed description and modifications will be apparent. The invention is defined by the claims that follow.

What is claimed is:

1. A microorganism culture medium comprising a derivative A' of a chromogen A, and a chromogen B,
    wherein the chromogen A is a chromogen being oxidized to a colorant, and the chromogen B is a chromogen being reduced to a colorant,
    the derivative A' acts as a substrate of an enzyme generated when a microorganism is growing, and is then converted to the chromogen A,
    and the derivative A' and the chromogen B are substantially not colored in the culture medium unless a microorganism is inoculated.

2. The microorganism culture medium of claim 1, wherein the derivative A' of the chromogen A is an oxyindole derivative or a halogen-substituted oxyindole derivative.

3. The microorganism culture medium of claim 1, wherein the chromogen B is a tetrazolium salt having a half wave potential of 300 mv or less as an absolute value.

4. The microorganism culture medium of claim 2, wherein the oxyindole derivative or the halogen-substituted oxyindole derivative is an acetic acid ester, a fatty acid ester, a phosphoric acid ester, a sulfuric acid ester or a glucoside.

5. The microorganism culture medium described in the claim 1, wherein the medium is a sheet type medium.

6. The microorganism culture medium described in claim 1, wherein the medium is an agar medium.

7. A method for detecting microorganisms using the medium described in claim 1.

* * * * *